United States Patent [19]
Han et al.

[11] Patent Number: 6,096,881
[45] Date of Patent: Aug. 1, 2000

[54] SULFUR TRANSFER REAGENTS FOR OLIGONUCLEOTIDE SYNTHESIS

[75] Inventors: Yongxin Han; Jimmy Tang, both of Framingham; Zhoada Zhang; Jin-Yan Tang, both of Shrewsbury, all of Mass.

[73] Assignee: Hybridon, Inc., Milford, Mass.

[21] Appl. No.: 08/865,666

[22] Filed: May 30, 1997

[51] Int. Cl.[7] .......................... C07H 21/00; C07H 21/02; C07D 285/01
[52] U.S. Cl. ........................ 536/25.3; 536/23.1; 548/123; 548/128
[58] Field of Search ................................ 536/23.1, 25.3; 548/123, 128

[56] References Cited

U.S. PATENT DOCUMENTS

| | | | |
|---|---|---|---|
| 3,753,908 | 8/1973 | de Vries et al. | 252/47.5 |
| 5,502,066 | 3/1996 | Heinemann et al. | 514/360 |

OTHER PUBLICATIONS

Chemical Abstracts, vol. 59, No. 6, Sep. 16, 1963, Columbus, Ohio, US; Abstract No. 6934e, M. Nagasawa et al., "Organophosporus insecticides containing sufonyl radicals" JP 62 015 649 A (Ihara Agricultural Chemical Co.) Oct. 1, 1960.

Chemical Abstracts, vol. 85, No. 25, Dec. 20, 1976, Columbus, Ohio, US; Abstract No. 187433p, T. Chiyonishio, "Effect of nematicides on the occurrence of black scurf of Chinese yam in sand dune fields", p. 112; Col. 1 and Tottori–Ken Nogyo Shikenjo Kenkyu Hokoku, vol. 13, 1973, pp. 29–52.

Chemical Abstracts, vol. 58, No. 10, May 13, 1963, Columbus, Ohio, US; Abstract No. 10125e, F. Cano et al., "S–Alkyl and arylsulfonylalkyl dithiophosphates" and IT 605 426 A (S.A.R.I.F.) May 27, 1960.

Chemical Abstracts, vol. 68, No. 7, Feb. 12, 1968, Columbus, Ohio, US; Abstract No. 28718t, T. Saito et al., "Systemic insecticidal properties of certain organic phosphorus compounds to the green peach aphid, *Myzus persicae*, and the tobacco cutworm, *Prodenis litura*", p. 2767, Col. 1 and Bochu Kaguku, vol. 31, No. 2, 1966, pp. 77–81.

Nucleic Acids Research, vol. 24, No. 9, May 1, 1996, XU Q et al., "Use of 1,2,4–dithiazolidine–3,5,–dione (DtsNH) and 3–ethoxy–1,2,4,–dithiazoline–5–one (EDITH) for synthesis of phosphorothioate–containing oligodeoxyribonucleotides", pp. 1602–1607.

Nucleic Acids Research, vol. 24, No. 18, Sep. 15, 1996, XU Q et al., "Efficient introduction of phosphorothioates into RNA oligonucleotides by 3–ethoxy–1,2, 4–dithiazoline–5–one (EDITH)", PP. 3643–3644.

Journal of Organic Chemistry, vol. 55, No. 15, Jul. 20, 1990, IYER, R.P. et al., "The Automated synthesis of sulfur–containing oligodeoxyribonucleotides Using 3H–1,2–Benzodithiol–3–one 1, 1,–Dioxide as a Sulfur–Transfer Reagent", pp. 4693–4699.

*Primary Examiner*—James O. Wilson
*Assistant Examiner*—Howard Owens
*Attorney, Agent, or Firm*—Hale & Dorr, LLP; Wayne A. Keown

[57] ABSTRACT

In our research, two commercially available compounds, 3-amino-1,2,4-dithiazole-5-thione (1) and xanthane hydride (2), and their derivatives 3–6 are found to be potential sulfur-transfer reagents. The efficiency and optimization of these new sulfur-transfer reagents were investigated by solid-phase syntheses of dinudeotide and oligonucleotide phosphorothioates. The results show that both compounds 1 and 2 are highly efficient sulfurizing reagents, and better than 99% sulfur transfer efficiency can be achieved at each step. In contrast to Beaucage reagent, these novel sulfur-transfer reagents are very stable in various solvents, and are available in bulk quantities at low cost. Due to these advantages, compounds 1 and 2 can be considered alternatives to Beaucage reagent, especially in large-scale preparation of oligonucleotide phosphorothioates. Furthermore, compounds 1 and 2 were modified to enhance their solubility in acetonitrile. Three types of structure, as described as Formulae I, II, and III, are considered as potential efficient sulfur-transfer reagents based on our results.

5 Claims, 8 Drawing Sheets

(STANDARD)

HPLC OF STANDARD DMT PROTECTED T-T PHOSPHOTHIOATE DIMER. HPLC WAS CARRIED ON A NOVA-PAK C18 COLUMN (60 Å, 3.9 X 150 mm) USING A LINEAR GRADIENT OF 0.1 M AQUEOUS $NH_4OAc$ AND $CH_3CN$-AQUEOUS $NH_4OAc$ (0.1 M) (4:1) FROM 1:9 TO 3:2 OVER A PERIOD OF 40 MIN, DETECTION AT 254 nm, FLOW RATE 1.0 ml/min. A: STANDARD P=S DIMER; B: COINJECTION OF P=S AND P=O DIMERS.

FIG. 1

HPLC OF DMT PROTECTED T-T PHOSPHOTHIOATE DIMER PREPARED USING 3-AMINO-1,2,4-DITHIAZOLE-5-THIONE AS SULFURIZING REAGENT. HPLC CONDITIONS AS FIGURE 1. SULFURIZATION WAS CARRIED OUT AT A CONCENTRATION OF 0.02 M IN PYRIDINE-$CH_3CN$ (1:9): A:4 EQUIV, 1 MIN (PURITY, 98.3%, P=O, 0.32%); B: 4 EQUIV, 5 MIN (PURITY, 98.5%; P=O, 0.28%); C: 12 EQUIV; 1 MIN (PURITY, 98.3%; P=O, 0.44%);; D: 12 EQUIV, 5 MIN (PURITY, 98.5%; P=O, 0.38%).

HPLC OF DMT PROTECTED T-T PHOSPHOTHIOATE DIMER PREPARED USING XANTHANE HYDRIDE AS SULFURIZING REAGENT. HPLC CONDITIONS AS FIGURE 1. SULFURIZATION WAS CARRIED OUT IN PYRIDINE - $CH_3CN$ (1:9) AT A CONCENTRATION OF 0.02 M (12 EQUIV) FOR 5 MIN. PURITY: 98.5%; P=O: 0.35%.

HPLC OF DMT PROTECTED T-T PHOSPHOTHIOATE DIMER PREPARED USING 3-N-ACTETYL-3-AMINO-1,2,4-DITHIAZOLE-5-THIONE AS SULFURIZING REAGENT. HPLC CONDITIONS AS FIGURE 1. SULFURIZATION WAS CARRIED OUT: A: 0.02 M (12 EQUIV) IN PYRIDINE-CH$_3$CN(1:9), 1 MIN (PURITY: 96.6%, P=O, 1.5%); B: : 0.02 M (12 EQUIV) IN CH$_3$CN, 5 MIN (PURITY: 96.6%, P=O, 1.5%).

HPLC OF DMT PROTECTED T-T PHOSPHOTHIOATE DIMER PREPARED USING 3-N-TRIMETHYLACETYL-3-AMINO-1,2,4-DITHIAZOLE-5-THIONE AS SULFURIZING REAGENT. HPLC CONDITIONS SAME AS FIGURE 1. SULFURIZATION WAS CARRIED OUT IN $CH_3CN$ AT A CONCENTRATION OF 0.06 M (12 EQUIV) FOR 5 MIN (PURITY: 90.7%; 1.09%).

ION-EXCHANGE HPLC OF SEQ ID NO:1 PREPARED USING 3-AMINO-1,2,4-DIAZOLE-5 THIONE (1) AS SULFURIZING REAGENT. HPLC CONDITIONS SEE GENERAL IN EXPERIMENTAL SECTION. SULFURIZATION WAS CARRIED OUT AT A CONCENTRATION OF 0.02 M (12 EQUIV) IN PYRIDINE-$CH_3CN$ (1:9): 1 MIN (PURITY, 80.7%; TOTAL P=O, 2.48%; 0.103% P=O PER STEP); B: 2 MIN (PURITY, 81.6%; TOTAL P=O, 2.38%; 0.099% P=O PER STEP).

SULFUR TRANSFER REAGENTS FOR OLIGONUCLEOTIDE SYNTHESIS

BACKGROUND OF THE INVENTION

1. Field of the Invention

The invention relates to the chemical synthesis of oligonucleotides and to chemical entities useful in such synthesis. More particularly, the invention relates to sulfurization of the internucleoside linkages of oligonucleotides.

2. Summary of the Related Art

Oligonucleotides have become indispensable tools in modern molecular biology, being used in a wide variety of techniques, ranging from diagnostic probing methods to PCR to antisense inhibition of gene expression. Oligonucleotide phosphorothioates are of considerable interest in nudeic acid research and are among the analogues tested as oligonudeotide therapeutics. Oligonucleotides phosphorothioates contain internucleotide linkages in which one of the nonbridging oxygen atoms of the phosphate group is replaced by a sulfur atom. This widespread use of oligonudeotides has led to an increasing demand for rapid, inexpensive, and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs*, pp. 165–189 (S. Agrawal, ed., Humana Press, 1993); *Oligonucleotides and Analogues: A Practical Approach*, pp. 87–108 (F. Eckstein, ed., 1991); and Uhlmann and Peyman, *Chemical Reviews*, 90: 543–584 (1990); Agrawal and Iyer, *Curr. Op. in Biotech.* 6: 12 (1995); and *Antisense Research and Applications* (Crooke and Lebleu, eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonudeotide synthesis. Reese, *Tetrahedron Lett.* 34: 3143–3179 (1978), discloses phosphotriester chemistry for synthesis of oligonucleotides and polynucdeotides. These early approaches have largely given way to the more efficient phosphoramidite and H-phosphonate approaches to automated synthesis. Beaucage and Carruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonudeotides by the H-phosphonate approach.

These latter approaches have been used to synthesize oligonudeotides having a variety of modified internudeotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager et al., *Biochemistry* 27: 7237 (1988), discloses synthesis of oligonucleotide phosphoramidates using phosphoramidite chemistry. Agrawal et al., *Proc. Natl. Acad. Sci. USA* 85: 7079–7083 (1988), discloses synthesis of oligonucleotide phosphoramidates and phosphorothioates using H-phosphonate chemistry.

Solid phase synthesis of oligonucleotides by each of the foregoing processes involves the same generalized protocol. Briefly, this approach comprises anchoring the 3'-most nucleoside to a solid support functionalized with amino and/or hydroxyl moieties and subsequently adding the additional nucleosides in stepwise fashion. Internucleoside linkages are formed between the 3' functional group of the incoming nucleoside and the 5' hydroxyl group of the 5'-most nucleoside of the nascent, support-bound oligonucleotide. In the phosphoramidite approach, the internucleoside linkage is a phosphite linkage, whereas in the H-phosphonate approach, it is an H-phosphonate internucleoside linkage. To create the sulfur-containing phosphorothioate internucleoside linkage, the phosphite or H-phosphonate linkage must be oxidized by an appropriate sulfur transfer reagent. In the H-phosphonate approach, this sulfurization is carried out on all of the H-phosphonate linkages in a single step following the completion of oligonucleotide chain assembly, typically using elemental sulfur in a mixed solvent, such as $CS_2$/pyridine. In contrast, the phosphoramidite approach allows stepwise sulfurization to take place after each coupling, thereby providing the capability to control the state of each linkage in a site-specific manner. Based on superior coupling efficiency, as well as the capacity to control the state of each linkage in a site-specific manner, the phosphoramidite approach appears to offer advantages.

Refinement of methodologies is still required, however, particularly when making a transition to large-scale synthesis (10 µmol to 1 mmol and higher). See Padmapriya et al., *Antisense Res. Dev.* 4: 185 (1994). Several modifications of the standard phosphoramidite processes have already been reported to facilitate the synthesis (Padmapriya et al., supra; Ravikumar et al., *Tetrahedron* 50: 9255 (1994); Theisen et al., *Nucleosides & Nucleotides* 12: 43 (1994); and Iyer et al., *Nucleosides & Nucleotides* 14: 1349 (1995)) and isolation (Kuijpers et al., *Nucl. Acids Res.* 18: 5197 (1990); and Reddy et al., *Tetrahedron Lett.* 35: 4311 (1994)) of oligonucleotides.

It is imperative that an efficient sulfur transfer reagent is used for the synthesis of oligonucleotide phosphorothioates via the phosphoroamidite approach. Elemental sulfur is not efficient due to poor solubility and slow sulfurization reaction. A number of more efficient sulfurizing reagents have been reported in recent years. These include phenylacetyl disulfide, (Kamer et al., *Tetrahedron Lett.* 30: 6757–6760 (1989)), H-1,2-benzodithiol-3-one-1,1-dioxide (Beaucage reagent)(Iyer et al., *J. Org. Chem.* 55: 4693–4699 (1990)), tetraethylthiuram disulfide (TETD)(Vu et al., *Tetrahedron Lett.* 32: 3005–3008 (1991)), dibenzoyl tetrasulfide (Rao et al., *Tetrahedron Lett.* 33: 4839–4842 (1992)), bis(O,O-diisopropoxyphosphinothioyl) disulfide (S-Tetra)(Stec et al., *Tetrahedron Lett.* 33: 5317–5320 (1993)), benzyltriethylammonium tetrathiomolybate (BTTM) (Rao et al., *Tetrahedron Lett.* 35: 6741–6744 (1994)), bis(p-toluenesulfonyl) disulfide (Effimov et al., *Nucl. Acids Res.* 23: 4029–4033 (1995)), 3-ethoxy-1,2,4-dithiazoline-5-one (EDITH)(Xu et al., *Nucleic Acid Res.* 24:1602–1607 (1996)), and 1,2,4-dithiazolidine-3,5-dione (DtsNH)(Xu et al., *Nucleic Acid Res.* 24:1602–1607 (1996)). Both Beaucage reagent and TETD are commercially available. Beaucage reagent has been widely used, however, its synthesis and stability are not optimal. In addition, the by-product formed by Beaucage reagent during sulfurization, 3H-2,1-benzoxanthiolan-3-one-1-oxide, is a potential oxidizing agent that can lead to undesired phosphodiester linkages under certain conditions. Therefore, its application in large-scale synthesis of oligonucleotide phosphorothioates may not be particularly suitable. We report two commercially available compounds 1 and 2 and novel analogues thereof as potential alternative sulfurizing reagents.

There is, therefore, a continuing need to develop new sulfur transfer reagents and processes for sulfurizing oligonucleotides. Ideally, such sulfur transfer reagents should be inexpensive to make, stable in storage, and highly efficient.

BRIEF SUMMARY OF THE INVENTION

The invention provides new processes for sulfur transfer reagents in sulfurizing oligonucleotides. The processes according to the invention yield inexpensive to make, stable in storage, and highly efficient in sulfurization.

In a first aspect, the invention provides novel sulfur transfer reagents having the structure according to Formula I:

Formula I wherein X is $R^1$, $NR^2R^3$, $NR^4COR^5$, $SR^6$, $OR^7$; each $R^1$, $R^2$, $R^3$, $R^4$, and $R^5$, is independently H or an alkyl or aromatic organic group; and each $R^6$ and $R^7$ is independently an alkyl or aromatic organic group.

In a second aspect, the invention relates to novel sulfur transfer reagents having the general structure according to Formula II:

Formula II wherein $R^8$ is H or an organic group; and $R^9$ is an organic group.

Another aspect of the invention provides for novel sulfur transfer reagents having the general structure according to Formula III:

Formula III wherein $R^{10}$ and $R^{11}$ are each independently H or an organic group.

In a fourth aspect, the invention provides novel processes for adding a sulfur group to an internucleoside linkage of an oligonucleotide using the novel sulfur transfer reagents according to the invention. In preferred embodiments, the novel processes according to the invention comprise contacting an oligonucleotide having at least one sulfurizable internucleoside linkage with a novel sulfur transfer reagent according to the invention for a time sufficient for sulfurization of the sulfurizable internucleoside linkage(s) to occur.

BRIEF DESCRIPTION OF THE DRAWINGS

FIG. 1A shows the HPLC of the standard P=S dimer. FIG. 1B shows the coinjection of P=S and P=O dimers.

FIG. 2A represents sulfurization conditions with 4 equiv, 1 min. FIG. 2B represents sulfurization conditions with 4 equiv, 5 min. FIG. 2C represents sulfurization conditions with 12 equiv, 1 min. FIG. 2D represents sulfurization conditions with 12 equiv, 5 min.

FIG. 6 shows the HPLC of SEQ ID NO:1 synthesized with compound 1 as a sulfur transfer reagent.

DETAILED DESCRIPTION OF THE PREFERRED EMBODIMENTS

The invention relates to the chemical synthesis of oligonucleotides and to chemical entities useful in such synthesis. More particularly, the invention relates to sulfurization of the internucleoside linkages of oligonucleotides. The patents and publications identified in this specification are within the knowledge of those skilled in this field and are hereby incorporated by reference in their entirety.

The invention provides new sulfur transfer reagents and processes for their use in sulfurizing oligonucleotides. The sulfur transfer reagents according to the invention are inexpensive to make, stable in storage, and highly efficient in sulfurization.

In a first aspect, the invention provides novel sulfur transfer reagents having the structure according to Formula I:

Formula I wherein X is $R^1$, $NR^2R^3$, $NR^4COR^5$, $SR^6$, $OR^7$; each $R^1$, $R^2$, $R^3$, $R^4$, and $R^5$, is independently H or an alkyl or aromatic organic group; and each $R^6$ and $R^7$ is independently an alkyl or aromatic organic group.

In a preferred embodiment, the sulfur transfer reagent having Formula I is 3-amino-1,2,4-dithiazole-5-thione (1), xanthane hydride (2), 3-N-acetyl-3-amino-1,2,4-dithiazole-5-thione (3), 3-N-trimethylacetyl-3-amino- 1,2,4-dithiazole- 5-thione (4), 3-N-benzoyl-3-amino-1,2,4-dithiazole-5-thione (5), or 3-N-benzenesulfonyl-3-amino-1,2,4-dithiazole-5-thione (6).

In a second aspect, the invention relates to novel sulfur transfer reagents having the general structure according to Formula II:

Formula II wherein R⁸ is H or an organic group; and R⁹ is an organic group.

Another aspect of the invention provides for novel sulfur transfer reagents having the general structure according to Formula III:

Formula III wherein each R¹⁰ and R¹¹ is independently H or an organic group.

In a preferred embodiment, the sulfur transfer reagent having Formula III is 3-amino-1,2,4-dithiazole-5-thione (1), xanthane hydride (2), 3-N-acetyl-3-amino-1,2,4-dithiazole-5-thione (3), 3-N-trimethylacetyl-3-amino-1,2,4-dithiazole-5-thione (4), 3-N-benzoyl-3-amino-1,2,4-dithiazole-5-thione (5), or 3-N-benzenesulfonyl-3-amino-1,2,4-dithiazole-5-thione (6).

The compounds 1 and 2, 3-amino-1,2,4-dithiazole-5-thione and xanthane hydride respectively, are commercially available from several chemical companies, including Lancaster, Crescent Chemicals, Maybridge, and TCI America. The purity of compounds 1 and 2 obtained is higher than 98%, and both compounds can be directly used in oligonucleotide synthesis without any additional purification. These compounds have been used in the rubber industry as vulcanization reagents. However, these compounds, to our best knowledge, have not been applied in the synthesis of oligonucleotides.

Derivatives of compound 1 may be easily synthesized. Starting from compound 1, 3-N-acetyl-3-amino-1,2,4-dithiazole-5-thione (3), 3-N-trimethylacetyl-3-amino-1,2,4-ithiazole-5-thione (4), 3-N-benzoyl-3-amino-1,2,4-dithiazole-5-thione (5), and 3-N-benzenesulfonyl-3-amino-1,2,4-dithiazole-5-thione (6) were conveniently prepared by solid-phase phosphoramidite approach in a better than 70% yield according to Scheme 1.

As explained in greater detail below, the reaction conditions included acetic anhydride/pyridine for 3 (96%); trimethyl acetic anhydride/Et₃N for 4 (70%); benzoyl chloride/Et₃N for 5 (70%); and benzene sulfonyl chloride/Et₃N for 6 (76%). The final products can be purified by a simple precipitation.

Stability and solubility studies of the sulfur transfer reagents were performed. Compounds 1–6 are stable in CH₃CN, pyridine-CH₃CN (1:9), and pyridine for more than one week. No precipitation occurred during testing period. All the testing reagents are stable during the operation of automatic DNA synthesizer, no clogging or other problems were observed during the syntheses.

Parent compounds 1 and 2 can be dissolved in CH₃CN to form a 0.01 M solution. Their solubility can be increased with addition of pyridine [0.02 M in pyridine-CH₃CN (1:9); 0.5 M in neat pyridine]. Derivatization of the parent compounds also can improve the solubility in CH₃CN (>0.02 M), e.g., compound 4 has a solubility better than 1 M in neat CH₃CN.

Accordingly, it has been demonstrated that the oligonucleotide phosphorothioates can be efficiently prepared by solid-phase phosphoramidite approach using 3-amino-1,2, 4-dithiazole-5-thione (1), xanthane hydride (2), and their corresponding derivatives. Compounds 1 and 2 are commercially available and relatively inexpensive compared with currently used sulfurizing reagents, such as Beaucage reagent and EDITH. Due to its high efficiency and low cost, compounds 1 and 2, and their appropriately modified analogues can be considered as an advantageous alternative to Beaucage reagent, especially in large-scale preparation of oligonucleotide phosphorothioates.

In another aspect, the invention provides novel processes for adding a sulfur group to an internucleoside linkage of an oligonucleotide using the novel sulfur transfer reagents according to the invention. In preferred embodiments, the novel processes according to the invention comprise contacting an oligonucleotide having at least one sulfurizable internucleoside linkage with a novel sulfur transfer reagent according to the invention for a time sufficient for sulfurization of the sulfurizable internucleoside linkage(s) to occur. Each sulfurizable internucleoside linkage preferably contains a phosphorous (III) atom. In a particularly preferred embodiment, the sulfurizable internucleoside linkage is a phosphite, thiophosphite, H-phosphonate, thio-H-phosphonate, or alkylphosphite (especially methylphosphite) internucleoside linkage. Preferably, the sulfurization reaction would be allowed to proceed to a sulfur transfer efficiency greater than that expected for the prior art compounds, as measured by $^{31}$P-NMR. In typical synthesis conditions such efficiency is achieved within from about 1 to about 5 minutes reaction time with the novel transfer reagents. Typically, the reaction takes place in pyridine, THF, or mixtures thereof. For purposes of this aspect of the invention, the term oligonucleotide includes linear polymers of two or more natural deoxyribonucleotide, ribonucleotide, or 2'-O-substituted ribonucleotide monomers, or any combination thereof. The term oligonucleotide also encompasses such polymers having chemically modified bases or sugars and/or non-nucleosidic analogs linked by phosphodiester bonds or analogs thereof ranging in size from a few monomeric units, e.g., 2–3, to several hundred monomeric units and/or having additional substituents, including without limitation lipophilic groups, intercalating agents, diamines and adamantane. In particular, oligonucleotides may also include non-natural oligomers having phosphorous-containing internucleoside linkages whose phosphorous (III) precursors are amenable to sulfurization, (See, e.g., Takeshita et al., *J. Biol. Chem* 282: 10171–10179 (1987).) For purposes of the invention, the term "2'-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halogen, hydroxy, trifluoromethyl, cyano, nitro, acyl, acyloxy, alkoxy, carboxy, carbalkoxy, or amino groups; or with a hydroxy, an amino or a halogen group, but not with a 2'-H group. Such oligonucleotides may include any of the internucleoside linkages which are known in the art, including without limitation phosphorothioate, phosphorodithioate, alkylphosphonate (especially methylphosphonate), phosphoramidate, amide (PNA), carbamate, and alkylphosphonothioate linkages. In a preferred embodiment, the oligonucleotide is bound to a solid support, but such oligonucleotides may be sulfurized in solution phase as well.

Figure 1:
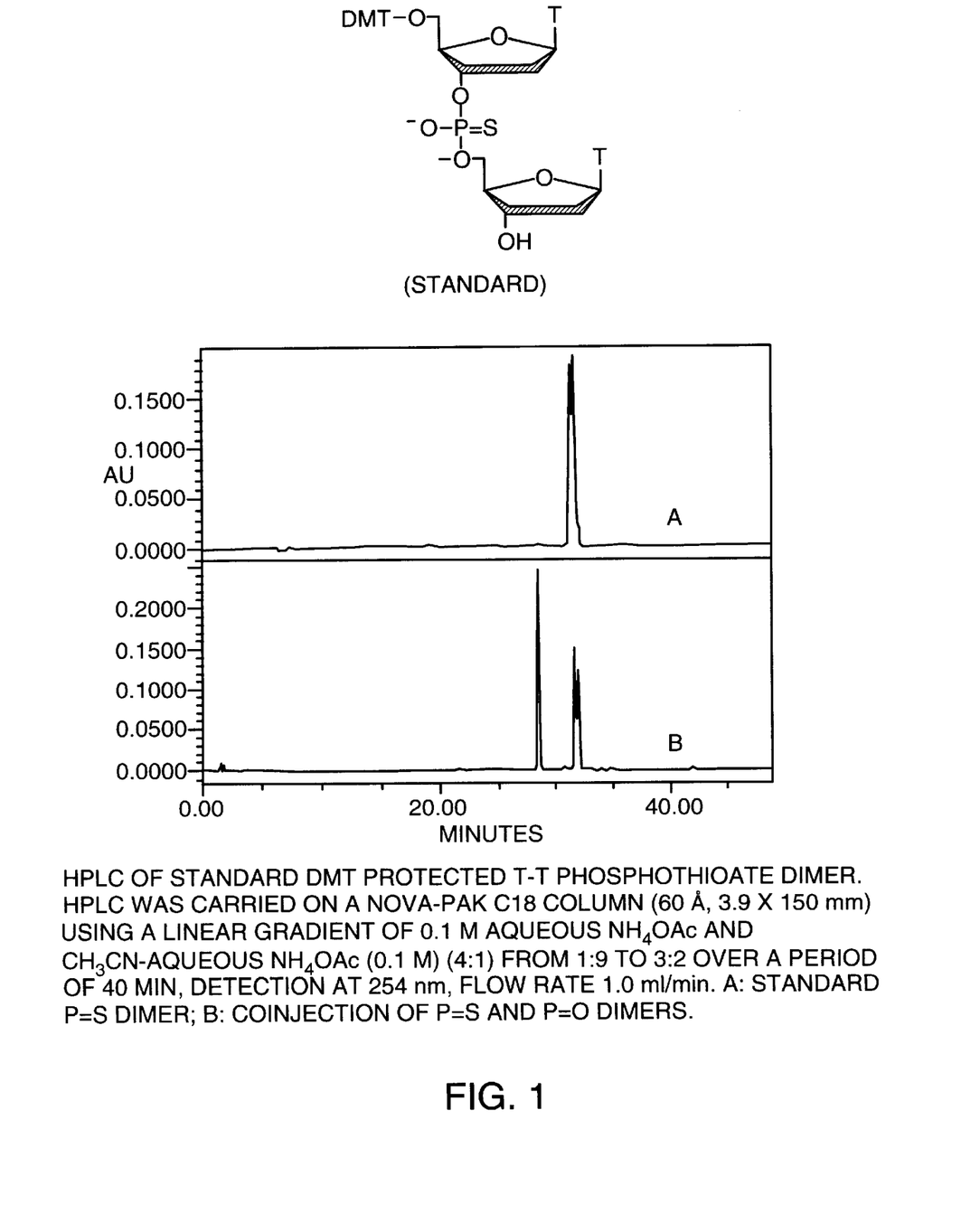
FIG. 1 shows the HPLC of the standard DMT protected T—T phosphothioate dimer.
Figure 2:
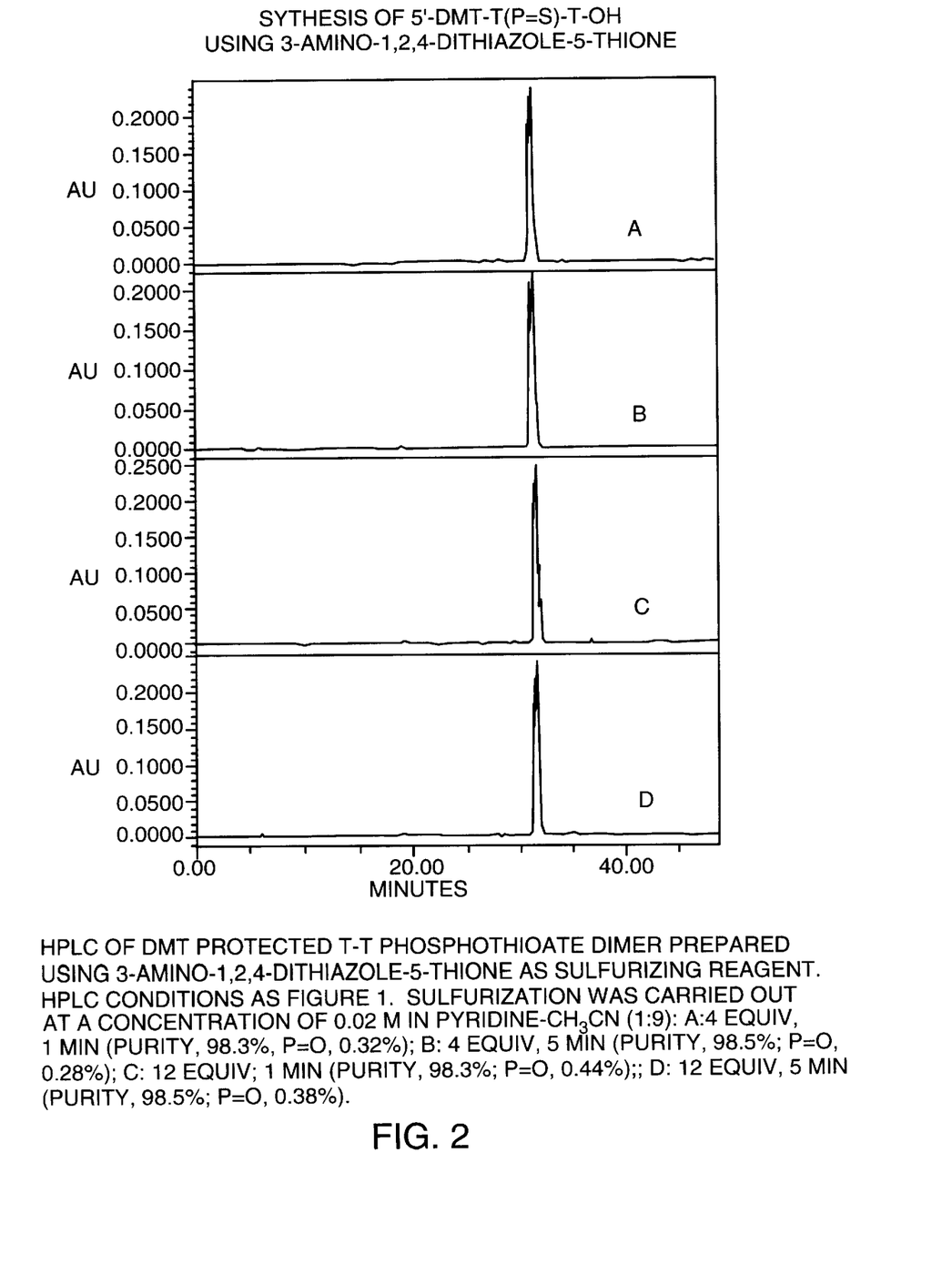
FIG. 2 shows the HPLC of DMT protected T—T phosphothioate dimer synthesized with compound 1 as a sulfur transfer reagent.
Figure 3:
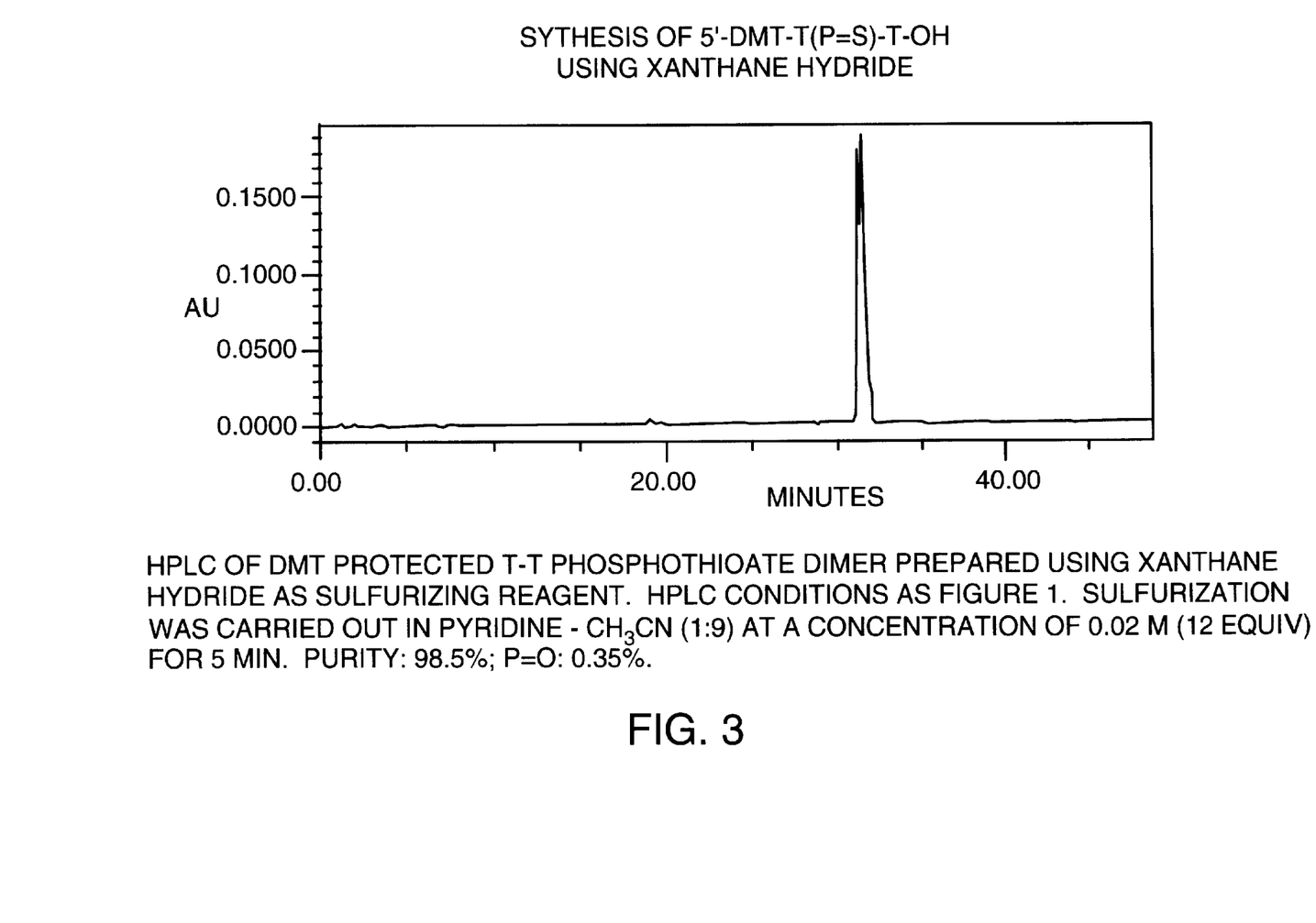
FIG. 3 is the HPLC of DMT protected T—T phosphothioate dimer prepared with compound 2 as a sulfur transfer reagent.
Figure 4:
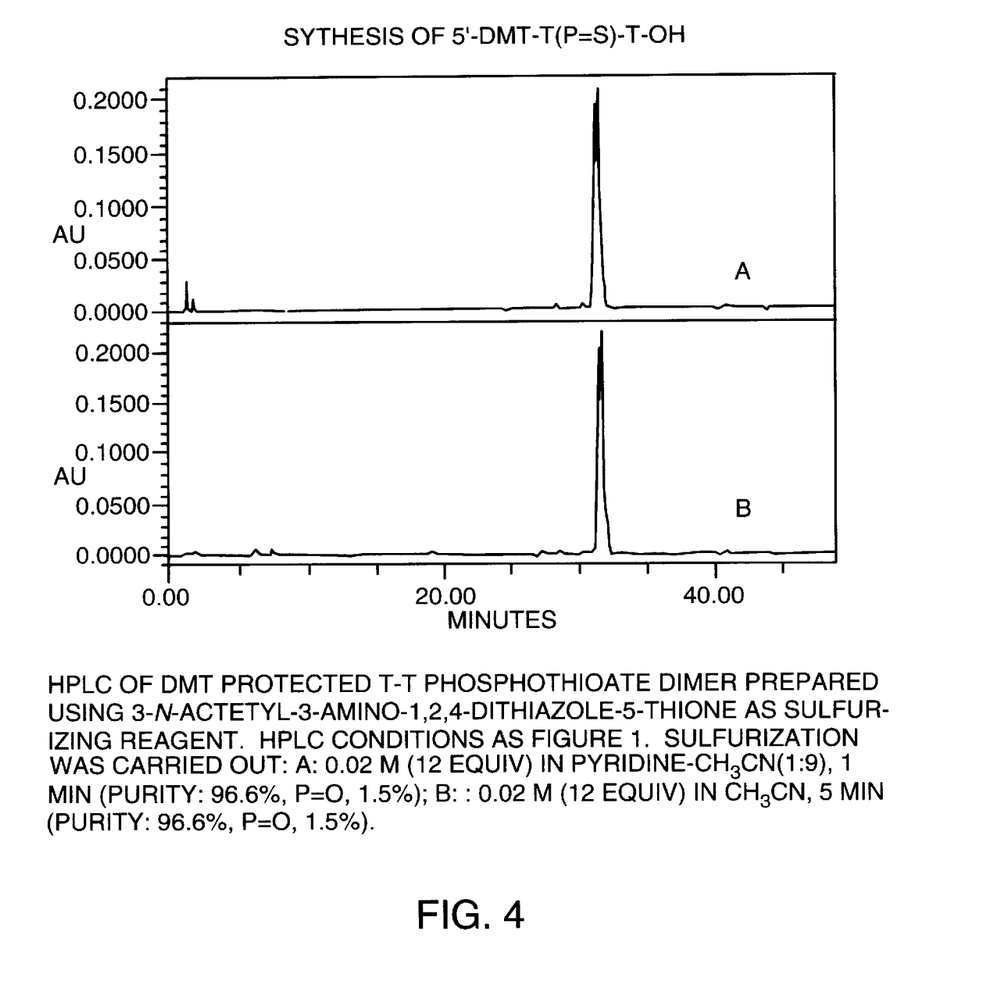
FIG. 4 is the HPLC of DMT protected T—T phosphothioate dimer prepared using compound 3 as a sulfur transfer reagent.
Figure 5:
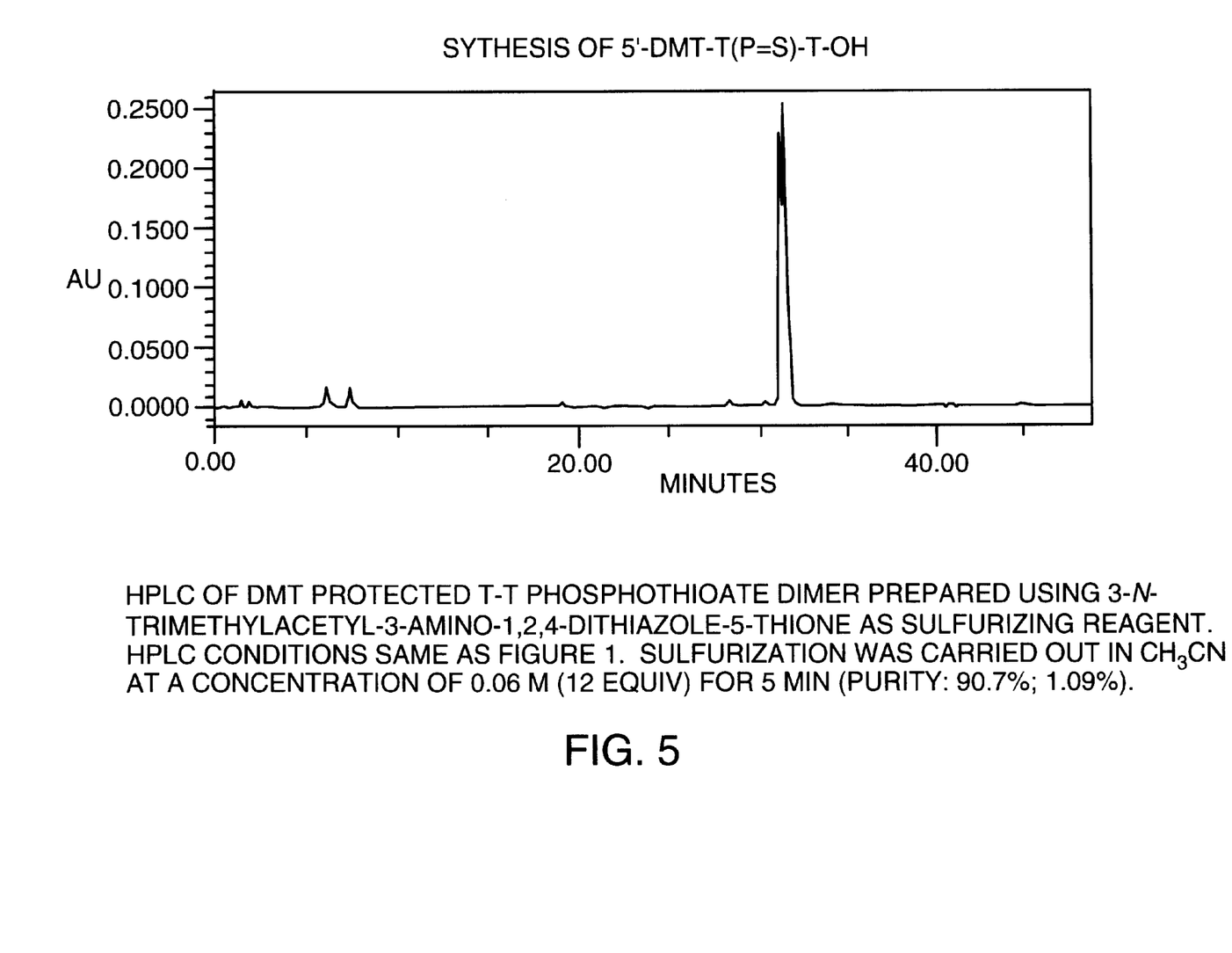
FIG. 5 is the HPLC of DMT protected T—T phosphothioate dimer synthesized with compound 4 as a sulfur transfer reagent.

The efficiency of these new sulfur-transfer reagents was first evaluated by solid-phase syntheses of dinucleotide phosphorothioate, 5'-DMT-TT-OH-3'. (FIG. 1.) Synthesis was performed at 1.0 μmol scale using the standard phosphorothioate protocol ("THIO 1 μmol"). The dinucleotide phosphorothioate was analyzed by reverse-phase HPLC. The results show that a better than 99% sulfur transfer efficiency was achieved using compounds 1 and 2. (FIGS. 2 and 3, respectively.) Compounds 3–4 were also found to be efficient sulfur-transfer reagents. (FIGS. 4–5.)

Figure 6A:
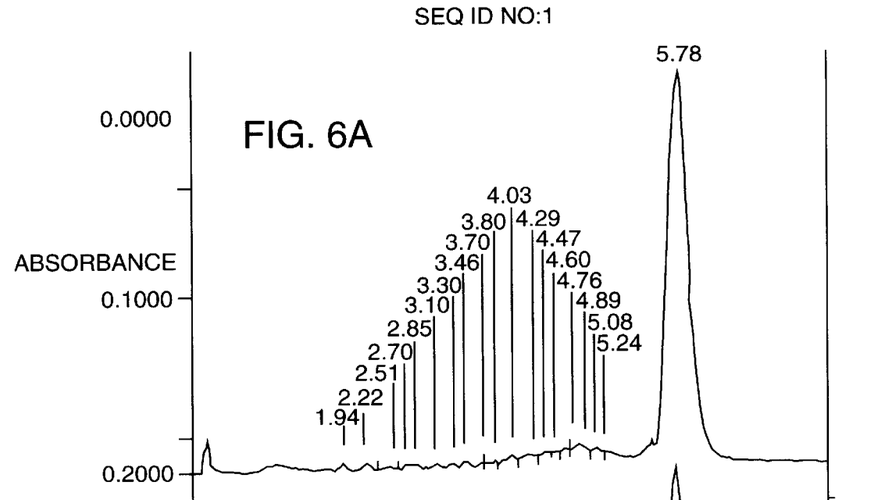
FIG. 6A represents 1 min of sulfurization in each synthetic cycle.
Figure 6B:
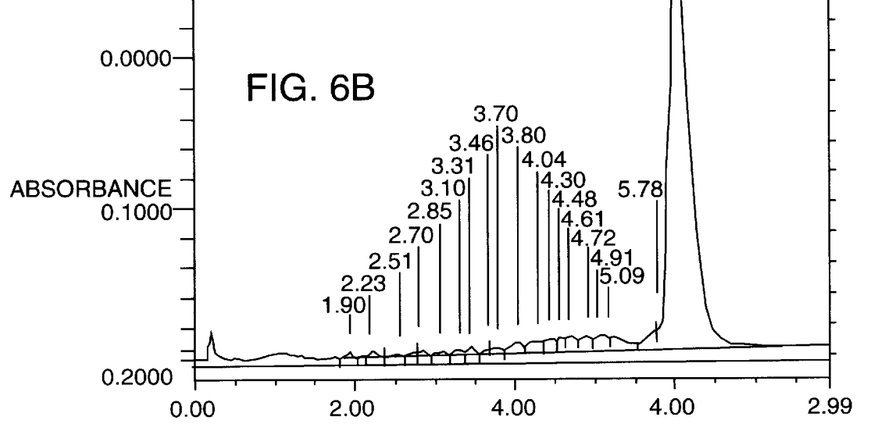
FIG. 6B represents 2 min of sulfurization in each synthetic cycle.
Figure 7:
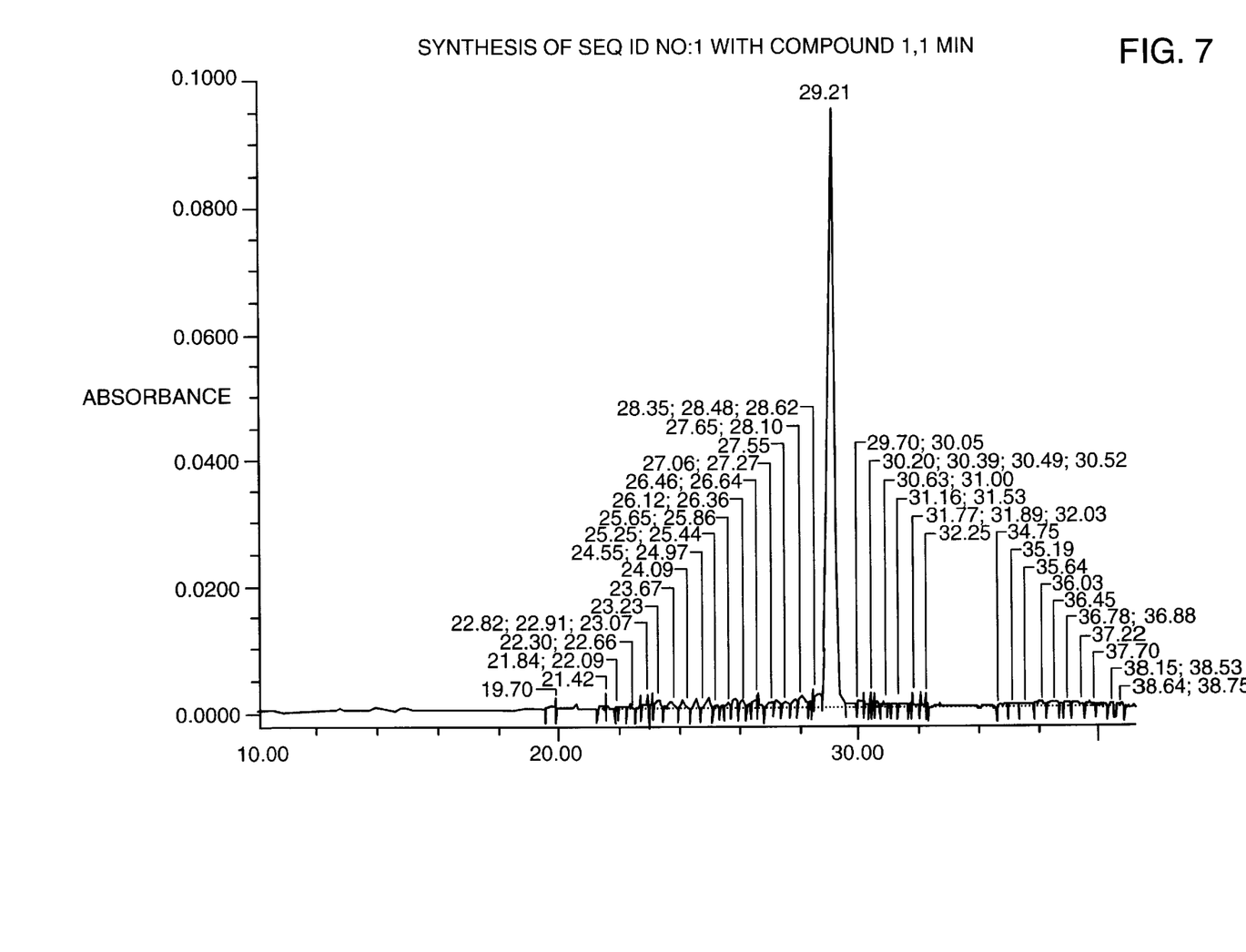
FIG. 7 represents the CE of SEQ ID NO:1 synthesized with compound 1 as a sulfur transfer reagent, where the sulfurization occurred for 1 min.
Figure 8:
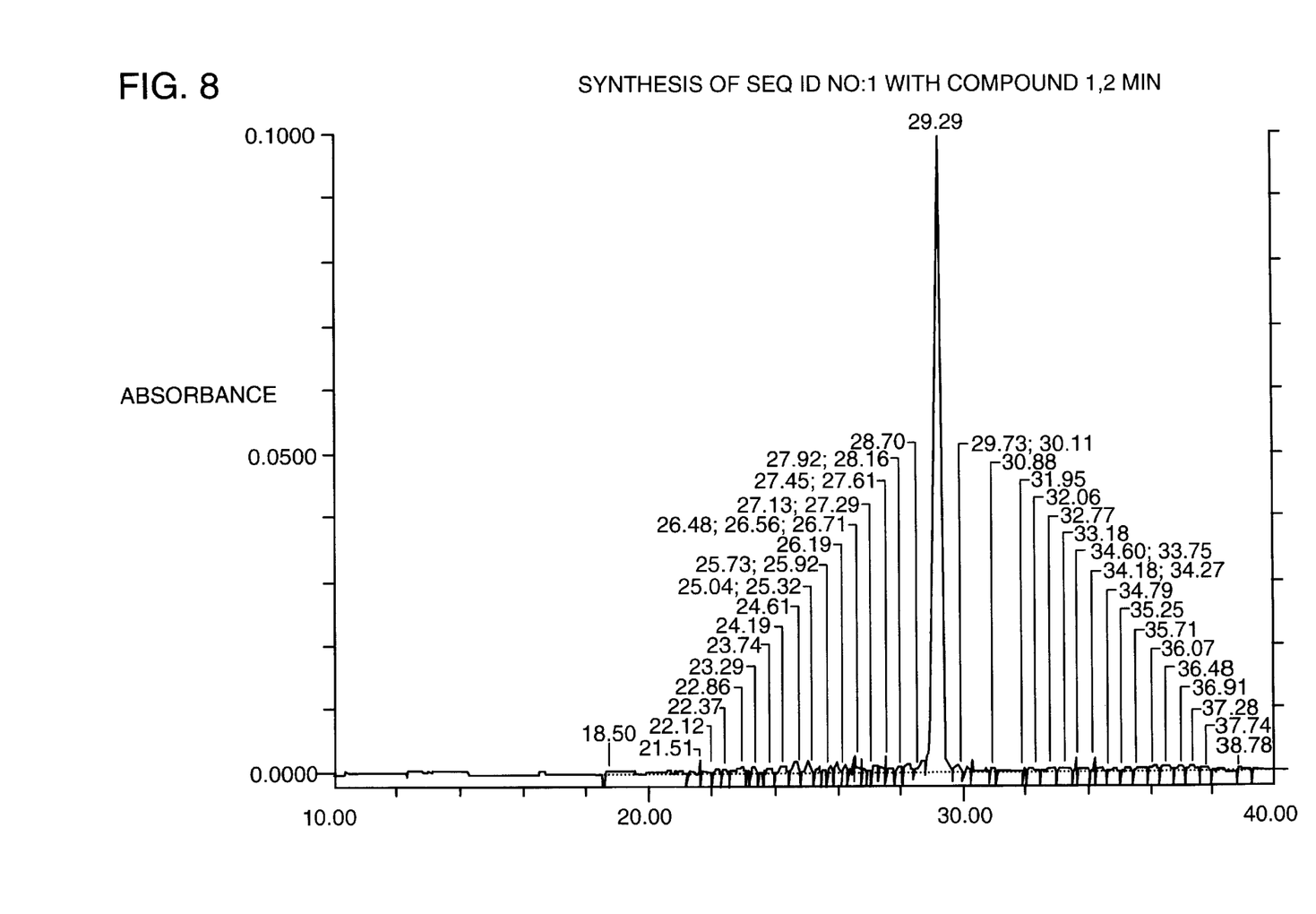
FIG. 8 represents the CE of SEQ ID NO: 1 synthesized with compound 1 as a sulfur transfer reagent, where the sulfurization occurred for 2 min.

To further evaluate the usefulness of compounds 1 and 2 as efficient sulfurizing reagents, an oligonucleotide phosphorothioate, 5'-CTCTCGCACCCATCTCTCCTTCT-3' (SEQ ID NO:1), was synthesized at 1.0 μmol scale using a 0.02 M solution in CH$_3$CN/pyridine (9:1) for 1 or 2 min of sulfurization in each synthetic cycle. After ammonolytic release from CPG and deprotection, the crude oligonucleotide phosphorothioate was analyzed by ion exchange-HPLC and CE. (FIGS. 6–8.) The results show that more than 99.5% sulfur transfer efficiency was achieved at each step, and a yield better than 80% has been achieved in these syntheses (see FIG. 3).

EXAMPLES

The following examples are intended to further illustrate certain preferred embodiments of the invention and are not intended to be limiting in nature.

In general, anhydrous pyridine and CH$_2$Cl$_2$ were purchased from Aldrich (Milwaukee, Wis.). Anhydrous CH$_3$CN was purchased from J. T. Baker Inc. (Phillipsburg, N.J.). dT-CPG, 5'-DMT-thymidine cyanoethyl phosphoramidite, Cap A, Cap B, activator, oxidizing and deblock solutions were purchased from PerSeptive Biosystems, (Framingham, Mass.). Beaucage reagent ($^3$H-1,2-benzodithiol-3-one-1,1-dioxide) was purchased from R. I. Chemical (Orange, Calif.). All other chemicals were purchased from Aldrich. $^{31}$P NMR spectra (121.65 MHZ) and $^1$H NMR spectra (300 MHz) were recorded on a Varian UNITY 300 (the chemical shift was correlated to 85% H$_3$PO$_4$ and tetramethylsilane, respectively). Dinucleotide and oligonucleotide syntheses were performed on an automated nucleic acid synthesizer (8909 Expedite™, Millipore, Bedford, Mass.). Reverse phase HPLC was performed on a Waters 600E pump with a Waters 440 absorbance detector, Waters 746 integrator, and a Nova-Pak C18 (3.9×150 mm) column, using a linear gradient of CH$_3$CN-aqueous NH$_4$OAc (0.1 M) (4:1) and 0.1 M aqueous NH$_4$OAc from 1:9 to 3:2 over a period of 40 min, flow rate 2 mL/min, detection at 260 nm. Ion-exchange HPLC analyses were performed on a Beckman System Gold 126 with a Beckman 166 absorbance detector on a NUCEOPAC PA-100 column (4×50 mm) using a linear gradient of Buffer A (25 mM of Tris-HCl and 1 mM EDTA, CH$_3$CN, pH=8) and Buffer B (2 M NaCl and buffer A) from 100% A to 100% B over a period of 5 min, then maintained at 100% B for 3 min, flow rate 2 mL/min, detection at 254 nm. Capillary electrophoresis was performed on a Beckman P/ACE System 5010. Samples were injected for 5 seconds and analyzed for 40 min.

The compound 3-amino-1,2,4-dithiazole-5-thione (1) was commercially available at 98% purity from several chemical companies, including Lancaster, Crescent Chemicals, and Maybridge, and can be directly used without further purification.

The compound xanthane hydride (2) was commercially available from TCI America at 98% purity, and can be directly used without any further purification.

Example 1

Synthesis of 3-N-acetyl-3-amino-1,2,4-dithiazole-5-thione (3)

Neat acetic anhydride (1.49 mL, 16 mmol) was added dropwise to the suspension of 3-amino-1,2,4-dithiazole-5-thione (compound 1, 2.0 g, 13 mmol) in the mixture of pyridine-$CH_3CN$ (1:5, 50 mL) over a period of 30 min. The resultant clear yellow solution was stirred at 25° C. for 1 h, then concentrated under reduced pressure. The resultant yellow solid was dissolved in EtOAc (500 mL), washed with 10% aqueous citric acid (500 mL), $H_2O$ (2×500 mL), then brine (500 mL), and then dried over $Na_2SO_4$. Evaporation of the organic solvent gave the title yellow solid. Yield: 2.50 g (96%); m.p. 229.6–230.1° C.

Example 2

Synthesis of 3-N-trimethylacetyl-3-amino-1,2,4-dithiazole-5-thione(4)

Neat trimethylacetic anhydride (3.20 mL, 16 mmol) was added to the suspension of 3-amino-1,2,4-dithiazole-5-thione (compound 1, 2.0 g, 13 mmol) in the mixture of $Et_3N$—$CH_2Cl_2$ (1:5, 30 mL) in one portion. A dear yellow solution was obtained in 10 min, and stirred at 25° C. for 2 h, and then concentrated under reduced pressure. The resultant yellow solid was dissolved in EtOAc (100 mL), washed with 10% aqueous citric add (2×100 mL), $H_2O$ (2×100 mL), then brine (100 mL), and then dried over $NA_2SO_4$. Organic solvent was removed under reduced pressure, the resultant yellow solid was treated with hexane (100 mL ) and stored at 4° C. for 2 h. The yellow precipitate was collected by filtration, washed with hexane (3×5 mL), and dried in vacuo. Yield: 2.17 g (70%); m.p. 179.6–179.6° C.

Example 3

Synthesis of 3-N-benzoyl-3-amino-1,2,4-dithiazole-5-thione(5)

3-Amino-1,2,4-dithiazole-5-thione (compound 1, 1.0 g, 6.6 mmol) was suspended in the mixture of $Et_3N$—$CH_2Cl_2$ (1:5, 20 mL), followed by addition of benzoic chloride (0.92 mL, 1.2 equiv). A dear yellow solution was obtained in 5 min. Reaction solution was stirred at 25° C. for 2 h, then concentrated under reduced pressure to remove organic solvent. The resultant yellow solid was treated with EtOAc (200 mL), the insoluble solid was removed by filtration, and the EtOAc layer was washed with 10% aqueous citric acid (2×200 mL), $H_2O$ (2×200 mL), brine (200 mL), and dried over $Na_2SO_4$. Evaporation of EtOAc gave a yellow solid, which was treated with $CH_2Cl_2$ (100 mL), then followed by addition of hexane (100 mL). The resultant solid was removed by filtration, and the filtrate was removed under reduced pressure to give a yellow solid. Yield: 1.17 g (70%).

Example 4

Synthesis of 3-N-benzenesulfonyl-3-amino-1,2,4-dithiazole-5-thione (6)

Except that benzene sulfonyl chloride was used instead of benzoic chloride, the reaction conditions and work-up process are identical to the preparation of compound 5. Yield: 1.46 g (76%).

Example 5

Stability and Solubility Studies of Xanthane Hydride, 3-Amino-1,2,4-dithiazole-5-thione, and Their Corresponding Derivatives in $CH_3CN$ The solubility and stability studies were carried out in $CH_3CN$, pyridine-$CH_3CN$ (1.9), and pyridine at 25° C. in all the cases. The saturated solution was dried, and the solubility was determined by the weight of the testing compounds in the exact volume of testing solution. The stability was determined based on either TLC or HPLC analyses.

Example 6

Synthesis of Dinucleotide Phosphorothioate

Dimer was assembled on a PerSeptive DNA/RNA (Millipore 8909 Expedite™, Millipore, Bedford, Mass.) on a 0.1 μmol scale using the synthesis protocol "THIO 1 μmol" (Expedite software version 1.01), starting from DMT-T-Su-CPG (500 Å, loading: 60 μmol/g). Sulfurizing reagents were prepared in either $CH_3CN$ or pyridine-$CH_3CN$ (1:9) at a concentration of 0.02 M unless specified. Sulfurization was carried out using 4 equiv or 12 equiv of sulfurizing reagents for 1 or 5 min reaction, respectively. Final cleavage was carried out by treatment using concentrated ammonium hydroxide (1 µmol/1 mL) at 25° C. for 1 h. CPG and other insoluble residues were removed by filtration, and the ammonium hydroxide solution was dried by lyophilization. HPLC analysis was carried out using a linear gradient of 0.1 M aqueous $NH_4OAc$ and $CH_3CN$-aqueous $NH_4OAc$ (0.1 M) (4:1) from 1:9 to 3:2 over a period of 40 min, flow rate 1.0 mL/min, detection at 260 nm. 5'-DMT-T(P=S)-T-OH-3' diastereomers were eluted at $t_R$=31.6 min and $t_R$=31.7 min. The corresponding P=O dimer was eluted at $t_R$=28.4 min. (FIG. 1.)

Example 7

Synthesis of a Oligonucleotide Phosphorothioate (5'-CTCTCGCACCCATCTCTCTCCTTCT-3' (SEQ ID NO:1))

The chain assembly was carried out using the same protocol as described in the dinucleotide phosphorothioate synthesis. Sulfurizing reagent compound 1) was prepared at a concentration of 0.02 M in pyridine-$CH_3CN$ (1:9), and sulfurization was carried out using 12 equiv for 1 or 2 min, respectively. Ion exchange HPLC and CE analyses were performed to evaluate the synthesis of this oligomer.

What is claimed is:

1. A sulfur transfer reagent selected from the group consisting 3-amino-1,2,4-dithiazole-5-thione, xanthane hydride, 3-N-acetyl-3-amino-1,2,4-dithiazole-5-thione, 3-N-trimethylacetyl-3-amino-1,2,4-dithiazole-5-thione, 3-N-benzoyl-3-amino-1,2,4-dithiazole-5-thione and 3-N-benzenesulfonyl-3-amino-1,2,4dithiazole-5-thione.

2. A process for adding a sulfur group to an internucleoside linkage of an oligonucleotide, the process comprising contacting an oligonucleotide having at least one sulfurizable internucleoside linkage with a sulfur transfer reagent according to claim 1 for a time sufficient for sulfurization of the sulfurizable internucleoside linkage to occur.

3. The process according to claim 2, wherein each sulfurizable internudeoside linkage contains a phosphorous (III) atom.

4. The process according to claim 3, wherein the sulfurizable internudeoside linkage is a phosphite, thiophosphite, H-phosphonate, thio-H-phosphonate, or alkylphosphite internucleoside linkage.

5. The process according to claim 4, wherein the sulfurization reaction is allowed to proceed from about 1 to about 5 minutes.

* * * * *